United States Patent [19]

Tang et al.

[11] Patent Number: 5,200,183

[45] Date of Patent: *Apr. 6, 1993

[54] RECOMBINANT BILE SALT ACTIVATED LIPASES

[75] Inventors: Jordan J. N. Tang; Chi-Sun Wang, both of Oklahoma City, Okla.

[73] Assignee: Oklahoma Medical Research Foundation, Oklahoma City, Okla.

[*] Notice: The portion of the term of this patent subsequent to Jul. 31, 2007 has been disclaimed.

[21] Appl. No.: 537,426

[22] Filed: Jun. 12, 1990

Related U.S. Application Data

[63] Continuation-in-part of Ser. No. 504,635, Apr. 4, 1990, abandoned, which is a continuation-in-part of Ser. No. 122,410, Nov. 19, 1987, Pat. No. 4,941,944.

[51] Int. Cl.$^5$ .................... A61K 37/54; C12N 15/55; C12N 9/20
[52] U.S. Cl. ................ 424/94.6; 435/198; 536/23.2; 536/24.31
[58] Field of Search ............ 536/27; 435/198; 424/94.6

[56] References Cited

U.S. PATENT DOCUMENTS 4,944,944 7/1990 Tang et al. ............ 424/94.6

OTHER PUBLICATIONS

Kyger et al., Biochem. Biophys. Res. Comm., vol. 164, No. 3 (Nov. 15, 1989), pp. 1302–1309.
Han et al., Biochemistry, vol. 26, 1617–1625 (1987).
Wang, Biochem. Biophys. Res. Comm., vol. 155, No. 2 (1988) pp. 950–955.
Young et al., PNAS USA, vol. 80 (Mar. 1983), 1194–1198.
Martin et al., Journal of Biological Chemistry, vol. 263, No. 22, 1988, pp. 10907–10914.
Chi-Sun Wang, et al., *Analytical Biochemistry* 133:457-461 (1983).

*Primary Examiner*—Jacqueline Stone
*Attorney, Agent, or Firm*—Kilpatrick & Cody

[57] ABSTRACT

The complete structure of human milk BAL cDNA is disclosed. The nucleotide sequences of the cDNA inserts of two clones overlap and together contain 2951 base pairs of BAL cDNA which codes for an open reading frame of 742 amino acid residues between initiation and termination codons. There is a putative signal sequence of 20 residues which is followed by a 61-amino-terminal sequence of BAL. The cDNA sequence also contains a 678-base 5'-untranslated sequence, a 97-base 3'-untranslated region, and a 14-base poly(A) tail. The deduced BAL protein structure contains in the carboxyl-terminal region fourteen repeating unis of 11 amino acids each. The repeating units have the basic structure of Pro-Val-Pro-Pro-Thr-Gly-Asp-Ser-Gly-Ala-Pro-, with only minor substitutions. The cDNA is useful for expression of protein, study of structure, function and the effect of modification or deletion or addition of amino acids, including entire repeating units, and as probes for studies involving BAL or related lipases, including rat pancreatic lysophospholipase, cholinesterase, and acetylcholinesterase.

10 Claims, 9 Drawing Sheets

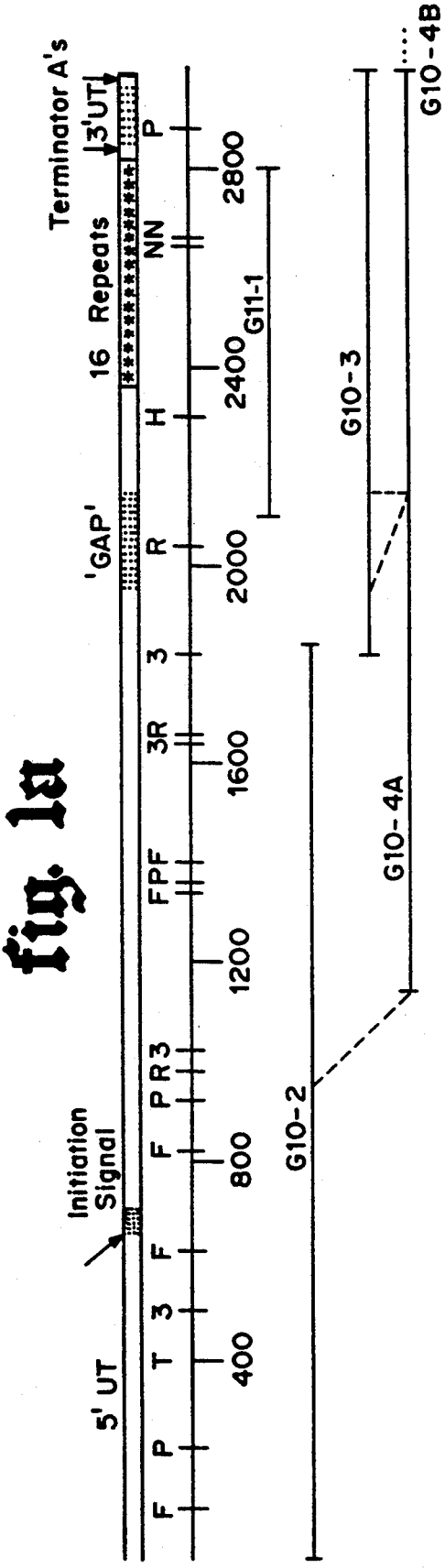
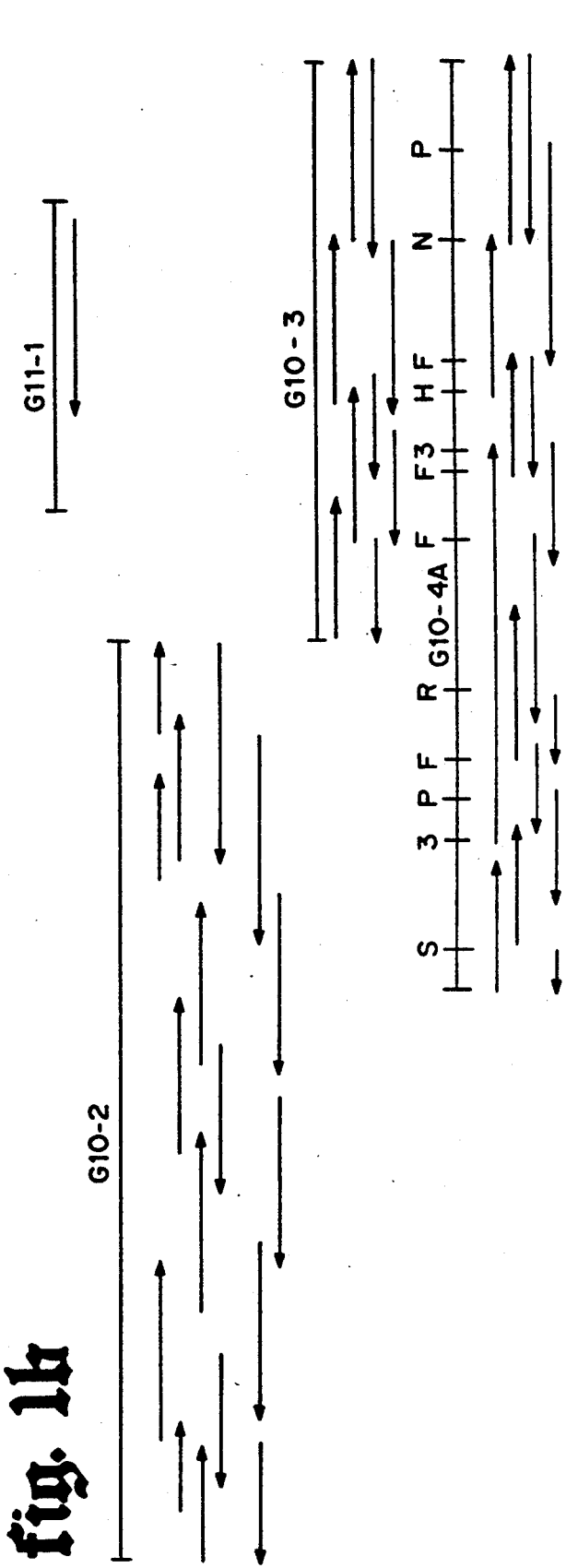
fig. 1a
fig. 1b

FIG. 2a

| | |
|---|---|
| CTCAATTGGAGGATCAAAGTTGAGAAAAGTAATATTCGACATTTTTCGATTCAACGGAGT | 60 |
| GGCCACCAAGACGATGTCATAGAAGTCTGAACGAGTCTCAGTTCCAATTTGGTAGACCAC | 120 |
| TTCATACATCTTTGTTGGATTTCCTGTGTACTTGGTCTTTGTTTTCTCCTCGATGTACAT | 180 |
| TACTGAGCCAGATATAAGATTGCTTTTGGATGCCTGCAGAAGCCCTGAGCAAACAAGTTT | 240 |
| ATTGCCACCTTCTACTGCCCAAAGGCCAGAATCAGAACAGGACAGTGACACCGCCCCCAC | 300 |
| AAAGGCATTGATGTCCGTGCTTTGGCCATAATTGACCCTCATAACAGGAGCAATCATTTC | 360 |
| ATTGAGGAACTTCTCAGAAAAGCCGGCCTTTTGCAAGGTTTCAAGAAGTGTTCGATTAAG | 420 |
| CATTCCAAGGAAGTCATCTCCTCCTAGAGCATGAAGTAATTTTTCGACACTACTGAAGGC | 480 |
| ATAGTCATGAGACTGGTAGCGGTAGATCCTCATGAACTTGTCTAACACGTCCTCTACCCA | 540 |
| CATGTGCATACGGAGGGATTGAAATCCATAGCGCCAAACTAATTTAATCACGTTAATTAT | 600 |
| GAACCAGTTGCTCTCCTCAAATACCAGAGTCTCTCCATTATATATCCCCAGTAGGCCACC | 660 |

```
                        MetGlyArgLeuGlnLeuValValLeuGlyLeuThrCysCys
CAGAGGCTGATGCTCACCATGGGGCGCCTGCAACTGGTTGTGTTGGGCCTCACCTGCTGC      720
                        1                             10
        TrpAlaValAlaSerAlaAlaLysLeuGlyAlaValTyrThrGluGlyGlyPheValGlu
        TGGGCAGTGGCGAGTGCCGCGAAGCTGGGCGCCGTGTACACAGAAGGTGGGTTCGTGGAA  780
                20                            30
        GlyValAsnLysLysLeuGlyLeuLeuGlyAspSerValAspIlePheLysGlyIlePro
        GGCGTCAATAAGAAGCTCGGCCTCCTGGGTGACTCTGTGGACATCTTCAAGGGCATCCCC  840
                40                            50
        PheAlaAlaProThrLysAlaLeuGluAsnProGlnProHisProGlyTrpGlnGlyThr
        TTCGCAGCTCCCACCAAGGCCCTGGAAAATCCTCAGCCACATCCTGGCTGGCAAGGGACC  900
                60                            70
        LeuLysAlaLysAsnPheLysLysArgCysLeuGlnAlaThrIleThrGlnAspSerThr
        CTGAAGGCCAAGAACTTCAAGAAGAGATGCCTGCAGGCCACCATCACCCAGGACAGCACC  960
                80                            90
        TyrGlyAspGluAspCysLeuTyrLeuAsnIleTrpValProGlnGlyArgLysGlnVal
        TACGGGGATGAAGACTGCCTGTACCTCAACATTTGGGTGCCCCAGGGCAGGAAGCAAGTC 1020
                100                           110
        SerArgAspLeuProValMetIleTrpIleTyrGlyGlyAlaPheLeuMetGlySerGly
        TCCCGGGACCTGCCCGTTATGATCTGGATCTATGGAGGCGCCTTCCTCATGGGGTCCGGC 1080
```

FIG. 2b

```
                120                                    130
HisGlyAlaAsnPheLeuAsnAsnTyrLeuTyrAspGlyGluGluIleAlaThrArgGly
CATGGGGCCAACTTCCTCAACAACTACCTGTATGACGGCGAGGAGATCGCCACACGCGGA     1140
                140                                    150
AsnValIleValValThrPheAsnTyrArgValGlyProLeuGlyPheLeuSerThrGly
AACGTCATCGTGGTCACCTTCAACTACCGTGTCGGCCCCCTTGGGTTCCTCAGCACTGGG     1200
                160                                    170
AspAlaAsnLeuProGlyAsnTyrGlyLeuArgAspGlnHisMetAlaIleAlaTrpVal
GACGCCAATCTGCCAGGTAACTATGGTCTTCGGGATCAGCACATGGCCATTGCTTGGGTG     1260
                180                 *        190        ●
LysArgAsnIleAlaAlaPheGlyGlyAspProAsnAsnIleThrLeuPheGlyGluSer
AAGAGGAATATCGCGGCCTTCGGGGGGGACCCCAACAACATCACGCTCTTCGGGGAGTCT     1320
                200                                    210
AlaGlyGlyAlaSerValSerLeuGlnThrLeuSerProTyrAsnLysGlyLeuIleArg
GCTGGAGGTGCCAGCGTCTCTCTGCAGACCCTCTCCCCCTACAACAAGGGCCTCATCCGG     1380
                220                                    230
ArgAlaIleSerGlnSerGlyValAlaLeuSerProTrpValIleGlnLysAsnProLeu
CGAGCCATCAGCCAGAGCGGCGTGGCCCTGAGTCCCTGGGTCATCCAGAAAAACCCACTC     1440
                240                                    250
PheTrpAlaLysLysValAlaGluLysValGlyCysProValGlyAspAlaAlaArgMet
TTCTGGGCCAAAAAGGTGGCTGAGAAGGTGGGTTGCCCTGTGGGTGATGCCGCCAGGATG     1500
                260                                    270
AlaGlnCysLeuLysValThrAspProArgAlaLeuThrLeuAlaTyrLysValProLeu
GCCCAGTGTCTGAAGGTTACTGATCCCCGAGCCCTGACGCTGGCCTATAAGGTGCCGCTG     1560
                280                                    290
AlaGlyLeuGluTyrProMetLeuHisTyrValGlyPheValProValIleAspGlyAsp
GCAGGCCTGGAGTACCCCATGCTGCACTATGTGGGCTTCGTCCCTGTCATTGATGGAGAC     1620
                300                                    310
PheIleProAlaAspProIleAsnLeuTyrAlaAsnAlaAlaAspIleAspTyrIleAla
TTCATCCCCGCTGACCCGATCAACCTGTACGCCAACGCCGCCGACATCGACTATATAGCA     1680
                320                                    330
GlyThrAsnAsnMetAspGlyHisIlePheAlaSerIleAspMetProAlaIleAsnLys
GGCACCAACAACATGGACGGCCACATCTTCGCCAGCATCGACATGCCTGCCATCAACAAG     1740
                340                                    350
GlyAsnLysLysValThrGluGluAspPheTyrLysLeuValSerGluPheThrIleThr
GGCAACAAGAAAGTCACGGAGGAGGACTTCTACAAGCTGGTCAGTGAGTTCACAATCACC     1800
                360                                    370
LysGlyLeuArgGlyAlaLysThrThrPheAspValTyrThrGluSerTrpAlaGlnAsp
AAGGGGCTCAGAGGCGCCAAGACGACCTTTGATGTCTACACCGAGTCCTGGGCCCAGGAC     1860
                380                                    390
ProSerGlnGluAsnLysLysLysThrValValAspPheGluThrAspValLeuPheLeu
CCATCCCAGGAGAATAAGAAGAAGACTGTGGTGGACTTTGAGACCGATGTCCTCTTCCTG     1920
                400                                    410
ValProThrGluIleAlaLeuAlaGlnHisArgAlaAsnAlaLysSerAlaLysThrTyr
GTGCCCACCGAGATTGCCCTAGCCCAGCACAGAGCCAATGCCAAGAGTGCCAAGACCTAC     1980
                420                                    430
AlaTyrLeuPheSerHisProSerArgMetProValTyrProLysTrpValGlyAlaAsp
GCCTACCTGTTTTCCCATCCCTCTCGGATGCCCGTCTACCCCAAATGGGTGGGGGCCGAC     2040
```

FIG. 2c

```
                440                          450
HisAlaAspAspIleGlnTyrValPheGlyLysProPheAlaThrProThrGlyTyrArg
CATGCAGATGACATTCAGTACGTTTTCGGGAAGCCCTTCGCCACCCCCACGGGCTACCGG  2100
                460                          470
ProGlnAspArgThrValSerLysAlaMetIleAlaTyrTrpThrAsnPheAlaLysThr
CCCCAAGACAGGACAGTCTCTAAGGCCATGATCGCCTACTGGACCAACTTTGCCAAAACA  2160
                480                          490
GlyAspProAsnMetGlyAspSerAlaValProThrHisTrpGluProTyrThrThrGlu
GGGGACCCCAACATGGGCGACTCGGCTGTGCCCACACACTGGGAACCCTACACTACGGAA  2220
                500                          510
AsnSerGlyTyrLeuGluIleThrLysLysMetGlySerSerSerMetLysArgSerLeu
AACAGCGGCTACCTGGAGATCACCAAGAAGATGGGCAGCAGCTCCATGAAGCGGAGCCTG  2280
                520                          530
ArgThrAsnPheLeuArgTyrTrpThrLeuThrTyrLeuAlaLeuProThrValThrAsp
AGAACCAACTTCCTGCGCTACTGGACCCTCACCTATCTGGCGCTGCCCACAGTGACCGAC  2340
                540                          550
GlnGluAlaThrProValProProThrGlyAspSerGluAlaThrProValProProThr
CAGGAGGCCACCCCTGTGCCCCCCACAGGGGACTCCGAGGCCACTCCCGTGCCCCCCACG  2400
                560                          570
GlyAspSerGluThrAlaProValProProThrGlyAspSerGlyAlaProProValPro
GGTGACTCCGAGACCGCCCCCGTGCCGCCCACGGGTGACTCCGGGGCCCCCCCCGTGCCG  2460
                580                          590
ProThrGlyAspSerGlyAlaProProValProProThrGlyAspSerGlyAlaProPro
CCCACGGGTGACTCCGGGGCCCCCCCCGTGCCGCCCACGGGTGACTCCGGGGCCCCCCCC  2520
                600                          610
ValProProThrGlyAspSerGlyAlaProProValProProThrGlyAspSerGlyAla
GTGCCGCCCACGGGTGACTCCGGGGCCCCCCCCGTGCCGCCCACGGGTGACTCCGGGGCC  2580
                620                          630
ProProValProProThrGlyAspSerGlyAlaProProValProProThrGlyAspSer
CCCCCCGTGCCGCCCACGGGTGACTCCGGGGCCCCCCCCGTGCCGCCCACGGGTGACTCC  2640
                640                          650
GlyAlaProProValProProThrGlyAspAlaGlyProProProValProProThrGly
GGCGCCCCCCCCGTGCCGCCCACGGGTGACGCCGGGCCCCCCCCCGTGCCGCCCACGGGT  2700
                660                          670
AspSerGlyAlaProProValProProThrGlyAspSerGlyAlaProProValThrPro
GACTCCGGCGCCCCCCCCGTGCCGCCCACGGGTGACTCCGGGGCCCCCCCCGTGACCCCC  2760
                680                          690
ThrGlyAspSerGluThrAlaProValProProThrGlyAspSerGlyAlaProProVal
ACGGGTGACTCCGAGACCGCCCCCGTGCCGCCCACGGGTGACTCCGGGGCCCCCCCTGTG  2820
                700                          710
ProProThrGlyAspSerGluAlaAlaProValProProThrAspAspSerLysGluAla
CCCCCCACGGGTGACTCTGAGGCTGCCCCTGTGCCCCCCACAGATGACTCCAAGGAAGCT  2880
                720
GlnMetProAlaValIleArgPheEnd
CAGATGCCTGCAGTCATTAGGTTTTAGCGTCCCATGAGCCTTGGTATCAAGAGGCCACAA  2940

GAGTGGGACCCCAGGGGCTCCCCTCCCATCTTGAGCTCTTCCTGAATAAAGCCTCATACC  3000

CCTGAAAAAAAAAAAAAAA                                           3018
```

FIG. 3a

```
          10                  30                   50
BAL   AKLGAVYTEGGFVEGVNKKLGLLG-DSVDIFKGIPFAAPTKA----LENPQPHPGWQGTLK
RPLL  .....L..............S...G.............TA-.T----.....R.........
CE    EDDIIIA.KN.K.R.M.--.TVFG-GT.TA.L...YAQ.PLGRLRFKK..SLTK.SDIWN 70                  90
      AKNFKKRCLQATITQD------------STYGDEDCLYLNIWVPQGRKQVSRDLPVMIWI
      .TD.............------------D...Q..................H.....V..
      ATKYANS.C.-N.D.SFPGFHGSEMWNPN.DLS.......V.I.APK---PKNAT.L...

110                 130                  150
      YGGAFLMGSGHGANFLNNYLYDGEEIATRGNVIVVTFNYRVGPLGFLS-TGDANLPGNYG
      ..........Q.....K...........................-..........F.
      ...G.QT.TS------SLHV...KFL.RVER....SM.....A....ALP.NPEA...M.

170                 190                  210
      LRDQHMAIAWVKRNIAAFGGDPNNITLFGESAGGASVSLQTLSPYNKGLIRRAISQSGVA
      ....................D...I........I.........................
      .F..QL.LQ..QK.......N.KSV........A.....HL...GSHS.PT...L...SF 230                 250                  270
      LSPWVIQKNPLF----WAKKVAEKVGCPVGDAARMAQCLKVTDPRALTL--AYKVPLAGL
      ....A..E....----...TI.K.....TE.T.K..G...I........--..RL..KSQ
      NA..AV--TS.YEARNRTLNL.KLT..SRENETEIIK..RNK..QEIL.NE.FV..YGT- 290                 310                  330
      EYPMLHYVGPVPVIDGDFIPADPINLYANAA--DIDYIAGTNNMDGHIFASIDMPAINKG
      ...IV..LA.I..V......D......D...--....L..I.D....L..TV.V...D.A
      --.L--S.N.G.TV....LTDM.DI.LELGQFKKTQILV.V.KDE.TA.LVYGA.GFS.D 350                 370
      NKKVT-----EED--FYKLVSEFTITKGLRGAKTTFDVYTESWAQDPSQENKKKTVVDF
      KQD..-----...--..R...GH.VA...K.TQA...I..............M.....A.
      .NSIITRKEFQ.GLKI.FPG....------.KESILFH..D-.VD.QRP..YREALG.V
```

```
390                 410                 430
ETDVLFLVPTEIALAQHRANAKSAKTYAYLFSHPSRMPVYPKWVGADHADDIQYVFGKPF
...I...I...M.......H........S...........I....M.......L........
VG.YN.AC.A-LEFTK-KFSEWGNNAFF.Y.E.R.SKLPW.E.M.VM.GYE.EF...L.L 450                 470                 490
ATPTGYRPQDRTVSKAMIAYWTNFAKTGDPNMGDSAVPTHWEPYTTENSGYLEITKKMGS
...L...A.................S......N.P.....Y...M..GN..D.N..IT.
ERRDN.TKAEEIL.RSIVKR.A....Y.N..ETQNN-S.S.PVFKSTEQK..—.LNTE.

510                 530                 550
SSMKRSLRTNFLRYWTLTYLALPTVTDQEATPVPPTGDSE-ATPVPPTGDSETAPVPPTG
T...EH..EK..KF.AV.FEM....VGD---HT..ED...-.A.....D..QGG.....D
TRIMTK..AQQC.F..-SF--F.K.--L.M.GNIDEAEW.WKAGFHRWNNYMMDWKNQFN 570                 590                 610
DSGAPPVPPTGDSGAPPVPPTGDSGAPPVPPTGDSGAPPVPPTGDSGAPPVPPTGDSAP
..QTT.....DN.Q.G--------------------------------------------
.YTSK-------------------------------------------------------

630                 650                 670
PVPPTGDSGAPPVPPTGDAGPPPVPPTGDSGAPPVPPTGDSGAPPVTPTGDSETAPVPPT
------------------------------------------------------------
------------------------------------------------------------

690                 710       722
GDSGAPPVPPTGDSEAAPVPPTDDSKEAQMPAVIRF
----------------------..V.....GP.G.
-----------------------..SCVGL
```

HUMAN MILK BILE SALT-ACTIVATED LIPASE (BAL)

| Repeat # | |
|---|---|
| 1 | PVPPTGDSEAT |
| 2 | PVPPTGDSETA |
| 3 | PVPPTGDSGAP |
| 4 | PVPPTGDSGAP |
| 5 | PVPPTGDSGAP |
| 6 | PVPPTGDSGAP |
| 7 | PVPPTGDSGAP |
| 8 | PVPPTGDSGAP |
| 9 | PVPPTGDSGAP |
| 10 | PVPPTGDAGPP |
| 11 | PVPPTGDSGAP |
| 12 | PVPPTGDSGAP |
| 13 | PVTPTGDSETA |
| 14 | PVPPTGDSGAP |
| 15 | PVPPTGDSEAA |
| 16 | PVPPTDDSKEA |

RAT PANCREATIC LYSOPHOSPHOLIPASE (RPLL)

| Repeat # | |
|---|---|
| 1 | HTPPEDDSEAA |
| 2 | PVPPTDDSQGG |
| 3 | PVPPTDDSQTT |
| 4 | PVPPTDNSQAG |

FIG. 3d

```
BAL  AKLGAVYTEG.GFVEGVNKKLGLLGDSVDIFK..GIPFAAPTKALENPQP      47
     . ...|...:| ..  : :. ... ::: .  |:|:|||. | :. |:
TG   ISTPSVHIDSFGQLQGGSQVVKVGTAWKQVYQFLGVPYAAPPLAENRFQA     445
     ....-  . .                        .....

--.-.----------                                ------
HP..GWQGTLKAKNFKKRCLQ.ATITQDSTYGDEDCLYLNIWVPQGRKQV          94
     ..  .|  |:.:|..::.|:| :| |  .|   ||||||::|| | .:
PEVLNWTGSWDATKLRSSCWQPGTRTPTPPQISEDCLYLNVFVPE...NL        492
     ..                                              -.

-----.                                       --
SRDLPVMIWIYGGAFLMGSGHGANFLNNYLYDGEEIATRGNVIVVTFNYR        144
     .: .|::::|... ||  . |:       ||. :|. ||:|||| |||
VSNASVLVFFHNTVEMEGSGGQLNI......DGSILAAVGNLIVVTANYR        536
     ....                                              ..

.-.----   ..-.                              -.
VGPLGFLSTGDANLPGNYGLRDQHMAIAWVKRNIAAFGGDPNNITLFGE.        193
     :|.. :|| |.-|..:::||:|| ||   |:-||. :|:||||..:||  ::
LGVFGFLSSGSDEVAGNWGLLDQVAALTWVQTHIGAFGGDPQRVTLAADR        586
                                                     ..

.                                                 ..
.SAGGASVSLQTLSPYNKGLIRRAISQSGVALSPWVI..QKNPLFWAKKV        240
     :|:.|;: |   . .| |:| :;: :| ||||| .| ...:  |
GGADVASIHLLITRPTRLQLFRKALLMGGSALSPAAIISPDRAQQQAAAL        636
     -.---------                                      .

----.. ------
AEKVGCPVGDAARMAQCLKVTDPRALTLAYKVPLAGLEYPMLHYVGFVPV        290
     |..||||:     :. |:| ...:. | |  ||  :    :|| :.|||
AKEVGCPNSSVQEVVSCFRQKPANILNEAQTKLLAVSG...PFHY...WGPV      682
     -----                                 .

.. ... -.---   -...---.-.
IDGDFIPADPINLY..ANAADIDYIAGTNNMDGHIFASIDMPAINKGNKK        338
     :||::::.. |  . .:  :..:|.:  |...|| . .:..:::| :
VDGQYLRELPSRRLKRPLPVKVDLLIGGSQDDGLINRAKAVKQFEESQGR       732
     -                .......                       ..
```

```
V.TEEDFYKLVSEFTITKGLRGAKTTFDVYTESWAQDPSQENKKKTVVDF    387
 . ....||.: :   ..:  :   . .::  |:..:|:.. .:|
TNSKTAFYQALQNSLGGEDSDARILAAAIWYYSLEHSTDDYASFSRALEN    782

....   .                                 ..  ....
ETDVLFLVPTEIALAQHRANAKSAKTYAYLFSHPSRMPVYPFWVGADHAD    437
 .|    .|::  :.:|   :   |...:. .::: .     .: |  :
ATRDYFIICPIVNMASLW..ARRTRGNVFMYHVPESYG....HGSLELLA    826

...   ..     .....         . ------------
DIQYVFGKPF..ATPTGYRPQDRTVSKAMIAYWTNFAKTGDPNMGD....    481
|:||.|| ||    |.. :.::...:|  :::.|:.||  ..|:|| ..
DVQYAFGLPFYSAYQGYFSTEEQSLSLKVMQYFSNFIRSGNPNYPHEFSQ    876

...                      . ....
..SAVPTHWEPYTTENSGYLEITKKMGSSSMKRS.LRTNFLRYWTLTYLA    528
 .. :|.  .|:.  : :|    |  |..|:.  .|  |:..  .:|. . .
KAAEFATPWPDFVPGAGG..ESYKELSAQLPNRQGLKKADCSFWSKYIQT    924

. . .      . .  ..  ..    .
LPTVTDQEATPVPPTGDSEATPVPPTGDSETAPVPPTGDSGAP           571
|.....:.:   ||.:  ..|  |.:::  |.:| |...|  ..
LKDADGAKDAQLTKSGEEDLEVGPGSEEDFSGSLEPVPKSYSK           967
```

FIG. 3e

RECOMBINANT BILE SALT ACTIVATED LIPASES

The United States government has certain rights in this invention by virtue of a grant from the National Institute of Health.

BACKGROUND OF THE INVENTION

This is a continuation-in-part of U.S. Ser. No. 07/504,635 entitled "Recombinant Bile Salt Activated Lipases", filed Apr. 4, 1990, abandoned, which is a continuation-in-part of U.S. Ser. No. 07/122,410 entitled "Dietary Compositions and Methods Using Bile Salt Activated Lipase" filed Nov. 19, 1987 by Jordan J. N. Tang and Chi-Sun Wang issued Jul. 31, 1990 as U.S. Pat. No. 4,944,944.

Human milk contains a bile salt-activated lipase (BAL) at a very high level of 0.5-1% of the milk protein, as described by Wang, "Fat Absorption" Vol. 1 Kuksis, editor pp. 83-117 (CRC Press, Inc., Boca Ratan, FL 1986) and Olivacrona and Bengtsson "Lipases", Borgstrom and Brockman, editors, pp. 205-261 (Elsevier, Amsterdam, The Netherlands 1984). The physiological role of BAL is to aid digestion of fats, especially triglycerides, to yield fatty acids and fatty acid salts.

Human BAL has been purified to homogeneity, as reported by Wang and Johnson, *Anal. Biochem*. 133, 457-461 (1983). As described in U.S. Ser. No. 07/061,883, it has now been discovered that this protein is the major rate-limiting-factor in fat absorption and subsequent growth by infants, particularly premature infants who are deficient in their own production of BAL, and that supplementation of formula with the purified enzyme significantly improves digestion and growth of these infants. This is clinically important in the preparation of baby formulas which contain relatively high percentages of triglycerides and which are based on plant or non-human milk protein sources, since babies fed these formulations are unable to digest the fats in the absence of added BAL.

The specificity and kinetics properties of BAL have been reported by Wang, et al., *J. Biol. Chem.* 256, 10198-10202 (1981); *J. Lipid Res.* 26, 824-830 (1985); *J. Biol. Chem.* 258, 9197-9202 (1983); and *Biochemistry* 27, 4834-4840 (1988). The binding of bile salts to BAL is essential for the specific hydrolysis of physiological substrates. Bile salts also participate in the substrate binding during the catalysis of BAL. These properties suggest that BAL comes from a distinct class of lipase apart from lipoprotein lipase and other pancreatic lipases.

It is therefore an object of the present invention to provide gene sequences encoding BAL for use in further analysis and characterization of the structure and function relationships of lipases.

It is another object of the present invention to provide gene sequences encoding BAL for use in preparing large quantities of BAL for inclusion in non-human milk infant formula.

It is a further object of the present invention to provide gene sequences encoding BAL in order to determine its structural relationship with other lipases and to provide a means for mutagenesis studies.

SUMMARY OF THE INVENTION

The complete structure of human milk BAL cDNA is disclosed. Eighteen cDNA clones of human milk bile salt-activated lipase (BAL) were identified from lactating human breast cDNA libraries in λgt11 and λgt10 using antibody and synthetic oligonucleotides as probes. Four clones were selected for sequence determination. The nucleotide sequences of the cDNA inserts of two clones overlap and together contain 3018 base pairs of BAL cDNA which codes for an open reading frame of 722 amino acid residues between initiation and termination codons. There is a putative signal sequence of 20 residues which is followed by a 722 residue amino-terminal sequence of mature BAL. The cDNA sequence also contains a 678-base 5'-untranslated sequence, a 97-base 3'-untranslated region, and a 14-base poly(A) tail. The sequence of one clone contains a deletion of 198 bases (Nos. 1966-2163) corresponding to 66 amino acid residues. The origin of this shorter version of cDNA is thought to be due to an alternative splicing during the processing of the BAL mRNA.

The deduced BAL protein structure contains in the carboxylterminal region sixteen repeating units of 11 amino acids each. The repeating units have the basic structure of Pro-Val-Pro-Pro-Thr-Gly-Asp-Ser-Gly-Ala-Pro-, with only minor substitutions.

The cDNA is useful for expression of BAL protein, which may be used to improve infant nutrition, to study structure, function and the effect of modification or deletion or addition of amino acids, including entire repeating units, and as probes for studies involving BAL or related lipases, including rat pancreatic lysophospholipase, cholinesterase, and acetylcholinesterase.

BRIEF DESCRIPTION OF THE DRAWINGS

FIG. 1 is a schematic presentation of the cDNA structure of human milk bile salt-activated lipase clones from lactating mammary gland.

FIG. 1A. BAL cDNA structure is established from four clones: G11-1, G10-2, G10-3, and G10-4, as shown horizontal lines. The bar on the top (FIG. 1A) represents the entire cDNA with different regions marked: 5'-untranslated region (5'UT), initiation codon, leader sequence, the repeating region (16 repeats), termination codon, 3'-untranslated region (3'UT), poly(A) tail (A's), and a "Gap" region which is a deletion in clone G10-4A. The relationships of G10-4A to other clones are indicated in dotted lines. The nucleotide numbers and restriction sites are shown on the second line. The keys to the restriction sites are: T, Taql; R, Rsal; H, Hhal; P, Pstl; and S, Smal; F, Hinfl; N, Narl; 3, Sau3Al.

FIG. 1B Schematic presentation of sequence data. Horizontal arrows represent the directions and the covering regions of the sequencing data.

FIGS. 2a, 2b and 2c show the cDNA and amino acid sequences of human milk bile salt-activated lipase. Nucleotide sequence is derived from clones G10-2 and G10-3 (FIG. 1). The nucleotide numbers are from 5' end and shown on the right margin of each line. The predicted amino acid sequence is numbered from the known amino terminus position of mature enzyme. A single potential N-linked glycosylation site is marked by an asterisk. The active site serine is marked by a diamond. The region of 198 nucleotides (1966 to 2163)

deleted in clone G10-4A ("Gap" region in FIG. 1) and the polyadenylation signal are underlined.

FIGS. 3a, 3b and 3c are a comparison of amino acid of various lipases.

FIGS. 3a and 3b shows the alignment of amino acid sequences of human milk bile salt-activated lipase (BAL), rat pancreatic lysophospholipase (RPLL), and cholinesterase (CE). Identical residues to BAL are marked with dots on RPLL and CE sequences and aligned spaces are represented by dashes.

FIG. 3c shows the alignment of sixteen internal repeating sequences of human milk BAL with the corresponding four internal repeats in RPLL.

FIGS. 3d and 3e compare primary and secondary structures of human bile salt-activated lipase (BAL, residues 1 to 571) and a region of rat thyroglobulin (TG, residues 396 to 967). The alignment of the two sequences was done with a computer program, developed by Devereux, et al., *Nucleic Acids Res.* 12(1), 387-395 (1984), based on creating maximum relationships. Four levels of relatedness between the corresponding residues in two sequences are shown between the sequences: identical residues, vertical lines; strongly similar, two dots; weekly similar, one dot; not related, unmarked. The computer generated secondary prediction based on Chou and Fasman, *Adv. in Enzymology* 47, 45-148 (1978), are shown above the BAL sequence and below TG sequence. The keys to the secondary structures: α-helix, squiggle; β-structure, solid line; turn, invert v; and random coil, dot. Boxed areas represent regions of the two sequences with strong secondary structural similarities.

DETAILED DESCRIPTION OF THE INVENTION

The present invention is the identification and characterization of at least two cDNAs encoding bile salt-activated lipase. The identification of the cDNAs provides the means to produce large scale quantities of BAL for supplementation of non-human milk formulas, the means to selectively modify the genes and proteins expressed therefrom, and the means to study and manipulate the structure and function of the proteins. The complete structure of human milk BAL cDNA and its relationship with rat pancreatic lysophospholipase (RPLL), acetylcholinesterase, cholinesterase and thyroglobulin are disclosed.

U.S. Ser. No. 07/122,410 filed Nov. 19, 1987, the teachings of which are incorporated herein, describes how the BAL is used in the preparation of nutritional formulations containing fat to aid in the digestion and utilization of the fat.

EXPERIMENTAL PROCEDURE

Materials.

Human milk BAL was purified as described by Wang and Johnson, *Anal. Biochem.* 133, 457-461 (1983). Rabbit antiserum against human BAL was prepared as reported by Wang, *J. Biol. Chem.* 256, 10198-10202 (1981). cDNA libraries from lactating human breast tissue in λgt11 and λgt10 were purchased from Clontech. Iodogen was purchased from Pierce Chemical Co. The radioisotopes, $^{125}$Iodine, $^{32}$P-ATP, $^{32}$P-dATP, $^{35}$S-dATP, and nylon filters (Hybond-N) were purchased from Amersham. The enzymes used in recombinant DNA manipulations were obtained from Bethesda Research Laboratory. The DNA sequencing kits and reagents were obtained from United States Biochemical and Boehringer. Other reagents were the highest grade commercially available and used without further purification.

METHODS

Isolation of amino-terminal CNBr-fragment of human milk BAL and amino-terminal sequence determination The cyanogen bromide cleavage of BAL (70 mg) was carried out using the conditions described by Steers et al., *J. Biol. Chem.* 240, 2478-2484 (1965). The heparin-binding CNBr-peptide was purified using affinity chromatography on a heparin-Sepharose column, as described by Wang and Johnson *Anal. Biochem.* 133, 457-461 (1983). In this procedure, the CNBr-fragments were applied onto a heparin-Sepharose column (2×10 cm) preequilibrated with 50 mM NH$_4$OH—HCl buffer, pH 8.5. The unretained fraction was eluted with 200 ml of the same buffer. The heparin-binding peptide, which was monitored by absorbance at 280 nm, was then eluted with the same buffer containing 0.3M NaCl. The fractions containing the heparin-binding peptide were pooled, lyophilized, redissolved with 1 ml of distilled water, and desalted on a Sephadex G-50 column (2×25 cm). The final yield of lyophilized heparin-binding peptide was about 4 mg. The heparin-binding fragment was judged to be pure by sodium dodecyl sulfatepolyacrylamide gel electrophoresis, using the method of Wang and Johnson (1983), with an apparent molecular weight of 12,000. The amino-terminal sequence of this fragment was determined by automated Edman degradation in a Beckman Sequencer Model 890 C. The PTH-amino acids were identified using a Waters Associates HPLC with a reverse-phase 5 μm C-18 column as described by Takahashi, et al., *J. Biol. Chem.* 258, 2819-2830 (1983). The 61-residue amino-terminal sequence of the peptide was determined to be: A K L G A V Y T E G G F V E G V N K K L G L L G D S V D I F K G I P F A A P T K A L E N P Q P H P G W Q G T L K A K N F K. The first 23 residues of this sequence are identical to the amino-terminal sequence for BAL reported by Wang and Johnson (1983) except that the 11th residue is glycine instead of lysine found in the current analysis. The above results also indicate that the heparin-binding sequence is located in the amino-terminal region of BAL.

Screening of cDNA libraries

About 5×10$^5$ plaques from a λgt11 cDNA library of lactating human breast tissue were screened at 22° C. with rabbit antibodies against human BAL. Rabbit antiserum against BAL was purified on an affinity column of immobilized human milk BAL on Sepharose 4B, using the method of Wang, et al., *Amer. J. Clin. Nutr.* 49, 457-463 (1983). The recovered antibodies were iodinated with $^{125}$iodine and Iodogen using the method of Markwell, et al., *Biochem.* 17, 4807-4817 (1978) and used to screen the library using the procedure of Huynh, et al., *DNA cloning* Glover, D. M., editor Vol. I, pp. 49-78 (IRL Press, Oxford 1985). For the screening of λgt10 library, about 10$^5$ plaques were transferred to Hybond-N membranes and probed with synthetic oligonucleotides using the plaque hybridization of Huynh, et al. (1985). Probe RP had the repeating unit sequence from clone G11-1 of the λgt11 library. Several other probes were designed and synthesized based on the 61-residue amino acid sequence of the amino-terminal CNBr-fragment. The oligonucleotides which produced positive results were: probe RP,5'-C C C C G G G C C T C A G T G G C A C C C G C G T-3', and probe NT1,5'-C T G C A G C A A A T G G G A T G C C C T T G / A A A G / A A T G / A T C C/ G A C-3' (based on amino-terminal sequence residues 30-37). A second screening of 6×10⁴ plaques of the λgt10 library was carried out using a Sau3Al fragment of clone G10-4A.

Subcloning and DNA sequence determination

Phage DNA from positive clones obtained from screening was prepared by the plate lysate method of Maniatis, et al., *Molecular Cloning, A Laboratory Manual* pp. 63-66 (Cold Spring Harbor Laboratories, Cold Spring Harbor, NY 1982), followed by the procedure of Bensen and Taylor, *BioTechniques* 126-127 (May/June 1984). cDNA inserts and their restriction fragments from the positive clones were subcloned using the method of Maniatis, et al., pp. 150-178 (1982), into pUC18, pUC19, M13mp18, and M13mp19 vectors. DNA sequencing using single or double strand templates was carried out using the dideoxynucleotide chain-termination method of Sanger, et al., *Proc. Natl. Acad. Sci. USA* 74, 5463-5468 (1977).

A total of 18 positive clones were identified from 3 different screenings. Five positive clones were obtained from human mammary gland cDNA library in λgt11 using BAL antibody as probe. From the λgt10 library, probes RP and NT1 produced three and two positive clones respectively. Eight positive clones were obtained from the same λgt10 library using as probe a 402-base pair Sau3Al fragment (nucleotides 1638 to 2237, without the 'gap' region, as described below) of a partial BAL cDNA obtained above (clone G10-4A). Restriction mapping combined with Southern blots of these clones suggested that all five λgt11 clones were related. The longest clone among these five, G11-1, was about 0.8 kbp. From the two screenings of the λgt10 library, the longest clones from each probe were: GT-2 (1.9 kbp, positive with probe NT1), clone G10-4 (4 kbp, positive with probe RP), and G10-3 (1.1 kbp, positive with the Sau3Al fragment of G10-4A). All four clones overlapped with each other as judged by the mapping and Southern blot results. These clones and various fragments from them were subcloned and the nucleotide sequences determined, as summarized in FIG. 1. Clones G10-2, G10-3 and the 5' side of an EcoRl fragment of G10-4 (G10-4A, 1.8 kbp) were completely sequenced (FIG. 1).

The 3' EcoRl fragment of G10-4 (G10-4B, 2.2 kbp) was downstream from the poly(A) sequence of BAL and is connected to G10-4A by an EcoRl linker sequence. Since G10-4B sequence is totally unrelated to that of BAL, it was clear that the G10-4A and G10-4B were inserted together into clone G10-4 during the ligation step of the library construction, so the sequence of G10-4B was not further studied. The partial sequence of G11-1 was identical to the 3'-region sequence of G10-3. Since the latter was completely sequenced, the sequencing of clone G11-1 was not continued.

Sequence data indicated that the human BAL cDNA sequence is contained in the combined sequence of clones G10-2 and G10-3 (FIGS. 1 and 2). This sequence (FIG. 2) contains an open reading frame which codes for 742 amino acid residues between the initation codon(nucleotides 669-671) and the stop codon (nucleotides 2905-2907). The reason that this particular Met codon is chosen as the initiation site, over another potential site upstream, is based on the presence of an optimal initiation flanking sequence, ACCATGG (nucleotides 666-672). Also, there are twenty predominately hydrophobic residues between this Met site and the amino-terminal position of the matured BAL (residue 1 in FIG. 2). The length of this 20-residue region is appropriate for the signal sequence of BAL. The amino-terminal 61 residues determined by Edman degradation are in complete agreement with the deduced amino acid sequence (FIG. 2, residues 1 to 61). There are 97 bases in the 3'-untranslated region between the termination codon and the 14-base poly(A) tail.

BAL cDNA sequence contains a region of sixteen highly similar, internally repeating sequences near the carboxyl-terminus (nucleotides 2353 and 2880). The deduced protein structure of this region forms 16 highly similar repeating units of eleven residues each (FIGS. 2 and 3). About one-third of the amino acids in this region are prolines, accounting for the high proline content of BAL. The amino acid composition of the deduced BAL sequence is compared with that from amino acid analysis in Table I. Human BAL is known to be a glycoprotein; a potential N-glycosylation site is observed at residue 187. The molecular weight of mature BAL calculted from the deduced sequence is 76,282.

The nucleotide sequence of clone G10-4A is identical to the corresponding region of the combined sequence from clones G10-2 and G10-3, as shown in FIG. 2, except that a section of 198 bases (nucleotides 1966 to 2163) is absent (FIGS. 1 and 2). This represents a deletion of 66 amino acids (residues 410 to 475). Several possible origins of this shorter cDNA have been considered. Since the nucleotide sequences of long and short cDNA's are otherwise identical, it suggests that they are the products of the same gene. A search of mRNA secondary structure near the 'gap' junctions did not provide any reason to suspect an erroneous copying by reverse transcriptase during the construction of cDNA. Also, the introduction of the 'gap' in the shorter cDNA did not change the reading phase. These facts seem to argue against the possibility that the shorter cDNA is a cloning artifact. The two versions of cDNA's are probably derived from a difference in the splicing of BAL and mRNA precursor. Although the gene structure of human BAL is not known, the sequence AAG (nucleotides 1963-1965) just before the 'gap' and the G's at both side of the junction at the end of the 'gap' (nucleotides 2163 and 2164) are the most favorable nucleotides for occurrence at intro/exon junctions, as reported by Padgett, et al., *Ann. Rev. Biochem.* 55, 119-1150 (1986). These structures are supportive for the alternative splicing explanation.

TABLE I

| Amino Acid Compositions of Human BAL as Predicted by cDNA Sequence | | | | | |
|---|---|---|---|---|---|
| | Derived from long cDNA sequence[a] | | Derived from short cDNA sequence[b] | | Purified BAL[c] |
| Amino Acid | No. of Res. | mol % | No. of Res. | mol % | mol % |
| Lys | 37 | 5.1 | 32 | 4.9 | 4.2 |
| His | 9 | 1.2 | 7 | 1.1 | 1.4 |
| Arg | 20 | 2.8 | 17 | 2.6 | 2.8 |
| Asp | 48 | 10.5 | 44 | 10.8 | 10.7 |
| Asn | 28 | | 27 | | |
| Thr | 59 | 8.2 | 53 | 8.1 | 8.5 |
| Ser | 41 | 5.7 | 37 | 5.6 | 5.1 |
| Glu | 25 | 6.0 | 25 | 6.3 | 4.9 |
| Gln | 18 | | 16 | | |

TABLE I-continued

Amino Acid Compositions of Human BAL as Predicted by cDNA Sequence

| Amino Acid | Derived from long cDNA sequence[a] No. of Res. | mol % | Derived from short cDNA sequence[b] No. of Res. | mol % | Purified BAL[c] mol % |
|---|---|---|---|---|---|
| Pro | 93 | 12.9 | 87 | 13.3 | 12.7 |
| Gly | 73 | 10.1 | 69 | 10.5 | 10.5 |
| Ala | 69 | 9.6 | 61 | 9.3 | 9.4 |
| Cys | 4 | 0.6 | 4 | 0.6 | 0.8 |
| Val | 53 | 7.3 | 49 | 7.5 | 8.0 |
| Met | 13 | 1.8 | 11 | 1.7 | 1.6 |
| Iso | 28 | 3.9 | 26 | 4.0 | 4.1 |
| Leu | 42 | 5.8 | 41 | 6.3 | 6.8 |
| Tyr | 26 | 3.6 | 20 | 3.0 | 3.3 |
| Phe | 25 | 3.5 | 21 | 3.2 | 3.9 |
| Trp | 11 | 1.5 | 9 | 1.4 | 1.3 |
| Total | 722 | | 656 | | |

[a]Based on the cDNA sequence without the deletion of 66 amino acid residues.
[b]Based on the cDNA sequence with the 66 amino acid deletion.
[c]Data taken from Wang, J. Biol. Chem. 256, 10198–10202 (1981).

COMPARISON of BAL cDNA sequence with other lipases

Human BAL sequence is highly similar to the sequence of rat pancreatic lysophospholipase (RPLL), reported by Han, J. H., Stratowa, C., and Rutter, W. J. (Biochemistry 26:1617–1625 (1987). There is 67% identity between the amino acid residues of the two enzymes (FIG. 3B the major difference is in the length of the repeating region. The closeness in structural homology of the two enzymes suggested that RPLL is the bile salt-activated lipase present in the pancreas. Limited amino-terminal sequence of human pancreatic carboxyl ester lipase (CEL) indicates that it is also homologous to BAL. In addition, BAL and CEL from different species have antibody cross-reactivity, consistent with close structural relationships. Based on the amino-terminal sequence data, porcine pancreatic cholesterol esterase (CHE) also appears to be identical to CEL. These structural comparisons suggest the possibility that pancreatic CEL and CHE are the same enzyme as RPLL, which appears to be the same as the bile salt-activated lipase present in pancreas. The structural information also suggests that BAL and RPLL represent a unique class of lipase since their structures are unrelated to the known structures of other lipases, including hepatic lipase, lipoprotein lipase and pancreatic lipase.

The most interesting structural feature of BAL and RPLL is the repeats of eleven residues of proline-rich sequences near the carboxyl-terminus of the enzymes. There are sixteen repeats in BAL and four repeats in RPLL (FIG. 3B). This type of repeating structure appears to be unique for these two enzymes since no other protein, including other lipases, in the protein database contains this repeating structure. Among the sixteen repeats in BAL, the repeat numbers three to ten are highly conserved, with the basic sequence of P V P P T G D S G A P. Two repeats at the beginning and three out of four repeats at the end contain more substitutions. Also, the sequence at the amino-terminal ends of each eleven residue unit are more conserved than that at the carboxyl-terminal ends (FIGS. 3B). The secondary structure prediction of this region reveals a strong tendency of open random coils. Although the function of this structural region is not known, the association of this unique structure with the unique function of bile salt activation of BAL and RPLL seems probable.

The amino acid sequence of BAL is also related to that of acetylcholinesterase, cholinesterase, and thyroglobulin. The alignment of choline esterase against BAL produces 27% of identical residues (FIG. 3A). Alignment of BAL with acetylcholinesterase produces similar results. The strongest homology in these sequence comparisons occurs in the region near the active site of the esterases (FIG. 3A). The sequence around the active-site serine, F G E S A G, in acetylcholinesterase is completely conserved in BAL (residue 194) and RPLL. These comparisons suggest that serine-194 in both BAL and RPLL are the active site residues; and the hydrolytic mechanism of the two lipases may also be related to that of the esterases. It is also of interest to note that the multiple mRNA of acetylcholinesterase resulted from alternative splicing, suggesting a possible relationship in regulation of activities in this family of enzymes.

The alignment of BAL against a region of thyroglobulin (residues 396 to 967) produces clear homology in several short stretches (FIG. 3C). However, the comparison of two proteins on their predicted secondary structures produces a close relationship throughout the entire length of BAL (FIG. 3C). These observations imply that this region of thyroglobulin is related to BAL in tertiary structure and that it is also an independently folded domain. The five proteins discussed above are probably diverged from a common ancestral protein in evolution.

Characterization of the heparin-binding region

The amino-terminal CNBr-fragment was shown to contain the heparin binding site of BAL, as described above. The amino acid sequence of this fragment (residues 1–101) was examined for potential heparin binding sequence, based on the known consensus heparin binding sequence of apolipoproteins and lipases reported by Martin, et al., J. Biol. Chem. 263, 10907–10914 (1988). No direct match of the motifs BBBXXB and BBXB (B=basic residues; X=uncharged residues) was found. However, a highly basic region with the pattern of BXBXXBBB is located between residues 56 and 63. This appears to be a potential heparin binding site of BAL.

Characterization of the two structural variants of BAL cDNA

The two structural variants of human BAL cDNA, if derived from alternative splicing and representing two different lengths of mRNA, would predict the presence of two sizes of BAL proteins in the human milk. A minor faster moving band which is consistent with the predicted molecular weight difference has been observed in sodium dodecyl sulfatepolyacrylamide gel electrophoresis of individual human milk BAL. Porcine pancreatic CEL also contains a smaller molecular weight version which has a size difference of about 9 kD. The two forms of the pig enzymes have the same amino-terminal sequence and their difference was not due to the carbohydrate or lipid content of the purified enzyme preparations, as reported by Rudd, et al., Biochim. Biophys. Acta 918, 106–114 (1987). It is therefore possible that the difference in these two forms of pig CEL is due to the same 'gap' observed in BAL.

Applications of the isolated cDNA for human BAL

The cDNA can be labelled for use as probes in assays or to screen for DNA encoding related proteins or proteins containing similar sequences. Methods for labelling DNA are well known to those skilled in the art, for example, as described by Maniatis, et al., *Molecular Cloning. A Laboratory Manual* (Cold Spring Harbor Laboratories, Cold Spring Harbor, NY 1982). Reagents for labelling sequences with fluorescent, radioactive, and enzymatic tags are all available commercially.

Cloning and structural determination of human BAL gene

The cDNA's of human BAL can also be used for the cloning and structural determination of human BAL gene or genes using methods known to those skilled in the art. A typical route to accomplish this is to screen a human genomic library (typically in lambda bacteriophage, commercially available by Clontech Laboratories, Inc., Palo Alto, CA) using oligonucleotides containing human BAL cDNA sequence. The probe can be a restriction enzyme fragment of human BAL cDNA. There are several proteins with amino acid sequence homology to BAL, such as pancreatic lipase or choline esterase, so the probe fragment can be used to recognize the genes of the homologous proteins. Since the amino acid sequences or the nucleotide sequences of most of these homologous proteins are known, as discussed with reference to FIG. 3, it is possible to select as the probe regions of BAL cDNA sequence where the differences to the genes of homologous proteins are the greatest. These probes can be chemically synthesized and used as probes to the human genomic lambda library. Positive lambda clones can be purified by secondary and tertiary plating and screening. The restriction mapping and DNA sequence determinations will reveal (a) how many human BAL gene(s), (b) the BAL gene structures (introns, exons, and regulatory elements), and (c) intron/exon junction positions in BAL cDNA's. The methods needed for carry out these works are described for the most part in Ausubel, F.M. et al., *Current Protocols in Molecular Biology* (John Wiley and Sons, N.Y. 1987)

Isolation of DNA encoding homologous proteins or regions

It is possible that more than one human BAL gene may be found since many proteins have multiple copies of genes. These genes, if they exist, should direct the synthesis of enzymes with very close structures and activities. BAL gene or genes may also be homologous to some other genes, such as that of acetylcholine esterase, choline esterase, pancreatic BAL, and thyroglobulin, which have amino acid sequences similar to human milk BAL. However, the structures of these proteins should be quite different from those of the BAL gene products.

There may be enzymes similar to BAL which have not yet been described. It should be possible to locate the cDNA or genes of these new enzymes by screening of genomic libraries using fragments of human BAL cDNA as probes. It is also possible that other yet undescribed proteins may contain segments very similar to the 16 repeats of human milk BAL for carrying out for some yet unspecified biological functions. The cDNA and genes of these proteins can also be identified by using cDNA fragments generated from the repeating region as probestor screening of libraries. The positive clones can be isolated and sequenced to estimate their relationships with BAL. The cDNAs or genes of any interesting proteins can be expressed and assessed for their possible biological functions. These all require using standard recombinant DNA technology and can be found in the reference cited above.

Expression of recombinant human BAL

Since in many eukaryotic expression systems exons are excised correctly, both human BAL cDNA and human BAL genomic DNA can be used to direct the synthesis of recombinant human BAL protein(s). Human BAL gene(s) are expected to contain in their untranslated region sequences which regulate the expression of the enzyme. These regulatory sequences may even be directly used in the transgenic animal expression.

Using recombinant DNA and genetic engineering technology, recombinant BAL protein can be produced from human BAL cDNA or genes by many different methods. These include the expression of BAL in hosts such as *E. coli*, Bacillus, yeast, funi, insect cells, mammalian cells, and transgenic animals. Since prokaryotic hosts cannot excise mammalian introns, it is preferrable to express the cDNA, with appropriate modifications, in procaryotic systems, rather than the gene. However, since procaryotes cannot glycosylate BAL, it is preferable to use eucaryotic systems for expression of BAL. When eukaryotic cells are used as hosts,either human BAL genes or cDNA can be used to direct the synthesis of the enzyme. They can also properly glycosylate BAL provided that a 'leader' or 'signal' sequence is present to direct newly synthesized BAL to the inside of the rough endoplasmic reticulum. Since the native BAL is a glycoprotein (Wang, C.S., *J. Biol. Chem.* 256:10198-10202, 1983), it may be important to use a host system that can glycosylate the protein properly.

It is possible that active human milk BAL activity can be derived by expressing only part of the cDNA or genes. It is well known that proteins contain some structure not essential for their biological, including enzymatic, activities. It is also possible that some of the amino acids in human milk BAL can be changed and the mutated BAL would still retain similar enzymic activities. Active fragments can be screened for using the same assays as used to measure activity of the intact enzyme. It is a routine procedure to synthesize fragments, then determine which fragments have activity. It is similarly routine to alter nucleotides within the sequences, express the protein and screen the protein for activity. This serves as a useful means for making BAL mutants having properties (enzymic activities, substrate specificities, physical properties, stabilities etc.) which provide advantages in the commercial use of the enzyme.

In all cases, the human BAL cDNA or gene can be inserted into appropriate expression vectors containing expression regulatory elements (such as transcription initiation signals, translation initiation signals, starting codon, termination codon, transcription terminating signals, polyadenylation signals, and others). Suitable vectors are commercially available from a variety of companies. After the recombinant vectors containing BAL cDNA or gene is transfected into the host cells, they may remain as extrachromosomal DNA or they may be integrated into the host genome. In either case, they may direct the synthesis of recombinant BAL in the host cells. Some examples for the expression of heterogous genes are described in *Methods in Enzymology*, Vol. 153, Chapters 23 to 34 (Editors, R. Wu and L. Grossman, Academic Press, 1987). Large scale culture of the BAL synthesizing host cells and the purification of the enzyme may form a cost effective commercial means of production of BAL. Methods are well known to those skilled in the art for the large scale production of enzymes. Some examples of potentially useful expression systems for BAL are given below:

(1) E. coli as host: Many mammalian cDNA's have been expressed in E. coli and many expression vectors with different promoters, operators, and other regulatory elements are available commercially. A typical vector construction and expression is described in: Lin, X. L. and Tang, J. J. Biol. Chem. 264:4482-4489 (1989). The expression of mammalian proteins in the cytosol of E. coli often produces insoluble 'inclusion bodies' and would require the refolding of recombinant protein. However, the use of a 'leader' sequence (such as omp, Duffaud, G. D., March, P. E., and Inouye, M. in Wu and Grossman (eds.) *Methods in Enzymology* 153:492-506 (1987)) will often direct the proper folding and also export of the recombinant BAL to the periplasmic space of the bacterial.

(2) Yeast as host: The principles for the expression of recombinant BAL in the yeast are similar to the for E. coli expression. Examples are provided by Bitter, G. A. et al. in *Methods in Enzymology* (Wu and Grossman, eds.) 153:516-544 (1987)). Like E. coli, yeast host cells may express a foreign gene either in the cytosol or as secreted protein. Unlike E. coli expression, the secreted expression in yeast is capable of glycosylation. This may represent an advantage for the expression of BAL since it is a glycoprotein.

(3) Fungi as host: There are small numbers of fungal expression vectors which have been successfully used to express heterogous genes. The existing fungal expression vectors integrate themselves into the host genome after transfection (Cullen, D., Gray, G. L., and Berka, R. M., Molecular Cloning Vectors for Aspergillus and Neurospora, in *A Survey of Molecular Cloning Vectors and their Uses*, (Butterworth Publishers, Stoneham, MA 1986). When a leader is present in front of the expressed protein codons, the secreted recombinant proteins can be glycosylated. Some examples of successful expressions involve bovine chymosin (Cullen, D. et al. Bio/Technology 5:369-378 (1987)) and an acid protease from a different fungus (Gray, G. L., Hayenga, K., Cullen, D., Wilson, L. J., and Norton, S. Gene 48:41-53 (1987)).

(4) Insect cells as host: Baculovirus expression vectors for the synthesis of foreign genes in insect cells have been successfully used to express many mammalian and viral proteins. This system is capable of glycosylation and can also express recombinant proteins at a high level. The use of this system has been reviewed in some detail (Luckow, V. A. and Summers, M. D., Trends in the Development of Baculovirus Expression Vectors, *Bio/Technology*, Sep. 11, 1987).

(5) Mammalian cells as host: Many mammalian cell expressions of heterogous genes have been successfully accomplished for commercial purposes. The commercial production of recombinant human tissue plasminogen activator is an example. Most of these expression vectors contains either mammalian promoter (such as metallocyanin or growth hormone) or viral promoters (such as SV40 early promoter or long terminal repeats of viral genes), polyadenylation signals, and appropriate regulatory elements for E. coli cloning including antibiotic resistance genes. After the insertion of BAL downstream from the promoter, the vector can be first cloned in E. coli, isolated and transfected into mammalian cells. Neomycin or similar resistant selection markers can be either cotransfected in another vector or in the same vector. For high level expression, a gene amplification system is advantageous. For example, the expression vector (or cotransfect) can contain the gene of dihydrofolate reductase (dhfr). When the dhfr- strain of Chinese hamster ovary (CHO) cells are used, the cloned gene can be coamplified with that of dhfr by adapting the transformed cells to increasing methotrexate concentration. The transformant clones secreting BAL can be identified by enzyme assays or by western blots. Successful examples of this approach include the synthesis of glycosylated recombinant prorenin (Poorman et al. Proteins 1:139-145 (1986)) and human immune interferon (Scahill, S. J. et al. *Proc. Natl. Acad. Sci., U.S.A.* 80:4654-4658 (1983)).

(6) Expression of BAL in transgenic animals: Technology already exists to transfer human BAL gene into the genomes of other animals for tissue specific expression (Jaenisch, R. *Science* 240:1468-1474 (1988); Westphal, H. FESEB J. 3:117-120 (1989)). Some works are already in progress to alter the composition of milk by using transgenic technology (for review, see: Bremel, R. D., Yom, H. C. and Bleck, G. T. J. *Dairy Sci.* 72:2826-2833 (1989)). The general approaches, as summarized in the three reviews listed above, is to construct vectors containing promoters of secretory mammary gland (milk) proteins (such as casein or milk lysozyme), human BAL cDNA or gene, and appropriate complementing elements. The cloned vector is then microinjected into a newly fertilized egg of cow or sheep and the egg transferred to a 'foster mother' for the fetal development and birth. The transgenic offsprings are analyzed for gene transfer by Southern blots and for the production of human BAL in the milk (cow and sheep do not produce BAL in milks). The transgenic animals can be interbred in order to produce a high yield strain.

Commerical applications for recombinant human milk BAL

The recombinant human milk BAL has a variety of uses. The enzyme can be used to supplement infant diet, as described in U.S. Ser. No. 07/122,410. The enzyme can be used to treat diseases. The enzyme can be used in industrial processes involving lipid digestion. The enzyme can be used in medical or clinical processes involved in lipid digestion. The enzyme may be used as research reagent (chemical) or a research tool (for the study of lipid digestion). Many of these applications were not possible before due to the extremely limited quantities of human BAL that could be extracted from human milk.

Modifications and variations of the present invention, recombinant DNA sequences encoding at least two forms of bile salt-activated lipase, and methods of use thereof, will be obvious to those skilled in the art from the foregoing detailed description of the invention. Such modifications and variations are intended to come within the scope of the appended claims.

We claim:

1. An isolated nucleotide molecule encoding bile salt-activated milk lipase or a polypeptide portion thereof, the lipase or portion thereof including a heparin binding sequence BXBXXBBB, wherein B is a basic amino acid residue and X is an uncharged amino acid residue, binding bile salts, and having lipase activity in the presence of the bile salts.

2. The molecule of claim 1 encoding a heparin binding amino acid fragment and hybridizing under standard conditions to the nucleic acid molecule in FIG. 2, nucleotides 739 to 1041.

3. The molecule of claim 1 encoding an amino acid sequence binding bile salts and hybridizing under standard conditions to the nucleic acid molecule in FIG. 2, nucleotides 2353 to 2814.

4. The molecule of claim 1 encoding one or more amino acid sequences selected from the group consisting of PVPPTGDSEAT, PVPPTGDSETA, PVPPTGDSGAP, PVPPTGDAGPP, PVTPTGDSETA, PVPPTGDSEAA, and PVPPTDDSKEA.

5. The molecule of claim 1 further comprising an initiation codon, nucleotides G C T G A T G, and a stop codon, T A G.

6. The molecule of claim 1 bound with a detection label.

7. a bile-salt activated milk lipase or polypeptide portion thereof, expressed in a procaryotic or yeast expression system, said lipase or portion thereof containing a heparin binding sequence BXBXXBBB, wherein B is a basic amino acid residue and X is an uncharged amino acid residue, binding bile salts and having lipase activity in the presence of the bound bile salts 8. The lipase of claim 7 in combination with a non-human milk nutritional solution including fats.

9. The lipase of claim 7 consisting essentially of the amino acid sequence shown in FIG. 2, amino acids 539 to 714.

10. The lipase of claim 7 including one or more amino acid sequences selected from the group consisting of PVPPTGDSEAT, PVPPTGDSETA, PVPPTGDSGAP, PVPPTGDAGPP, PVTPTGDSETA, PVPPTGDSEAA, and PVPPTDDSKEA.

* * * * *